(12) United States Patent
Choi et al.

(10) Patent No.: US 11,253,266 B2
(45) Date of Patent: Feb. 22, 2022

(54) SLEEVE FOR DELIVERY OF EMBOLIC COIL

(71) Applicant: ENDOSHAPE, INC., Boulder, CO (US)

(72) Inventors: Steve Choi, Lafayette, CO (US); Jessi Watson, Denver, CO (US); Gregory Edwin Mirigian, Dublin, CA (US)

(73) Assignee: ENDOSHAPE, INC., Boulder, CO (US)

( * ) Notice: Subject to any disclaimer, the term of this patent is extended or adjusted under 35 U.S.C. 154(b) by 547 days.

(21) Appl. No.: 16/641,988

(22) PCT Filed: Aug. 25, 2016

(86) PCT No.: PCT/US2016/048715
§ 371 (c)(1),
(2) Date: Feb. 25, 2020

(87) PCT Pub. No.: WO2017/035365
PCT Pub. Date: Mar. 2, 2017

(65) Prior Publication Data
US 2020/0268392 A1 Aug. 27, 2020

Related U.S. Application Data

(60) Provisional application No. 62/209,736, filed on Aug. 25, 2015.

(51) Int. Cl.
*A61B 17/12* (2006.01)
*A61B 17/00* (2006.01)

(52) U.S. Cl.
CPC .... *A61B 17/1214* (2013.01); *A61B 17/12109* (2013.01); *A61B 2017/0023* (2013.01);
(Continued)

(58) Field of Classification Search
CPC .......... A61B 17/1214; A61B 17/12109; A61B 2017/00336; A61B 2017/1205;
(Continued)

(56) References Cited

U.S. PATENT DOCUMENTS 5,350,397 A * 9/1994 Palermo ........... A61B 17/12022
606/200
6,350,270 B1 * 2/2002 Roue ................ A61B 17/12022
606/151
(Continued)

FOREIGN PATENT DOCUMENTS

WO 2010096541 A1 8/2010

OTHER PUBLICATIONS

European Patent Office, "Examination Report for App. No. 16762928. 6, dated Feb. 27, 2020", 6 pages.
(Continued)

*Primary Examiner* — Kelly J Bekker
*Assistant Examiner* — Paige A Codrington
(74) *Attorney, Agent, or Firm* — Bochner IP, PLLC; Andrew D. Bochner

(57) ABSTRACT

An endovascular treatment system includes a delivery sleeve that is insertable into an intravascular catheter. A therapeutic device is housed coaxially within the delivery sleeve and both are advanced within the catheter in combination. An advancement mechanism is connected to the therapeutic device to advance the therapeutic device out of the delivery sleeve and into a patient. The delivery sleeve includes a stop positioned on the proximal end. The stop contacts the proximal end of the catheter, limiting the distance the delivery sleeve is inserted into a catheter.

16 Claims, 8 Drawing Sheets

(52) U.S. Cl.
CPC ............... *A61B 2017/00336* (2013.01); *A61B 2017/00845* (2013.01); *A61B 2017/1205* (2013.01); *A61B 2017/12054* (2013.01)

(58) Field of Classification Search
CPC . A61B 2017/12054; A61B 2017/12095; A61F 2/95; A61F 2/962; A61F 2/966
USPC ........................................................ 606/200
See application file for complete search history.

(56) References Cited

U.S. PATENT DOCUMENTS

| | | | | |
|---|---|---|---|---|
| 9,375,333 | B1* | 6/2016 | Aboytes | A61B 17/12109 |
| 2002/0121472 | A1 | 9/2002 | Garner et al. | |
| 2003/0236517 | A1* | 12/2003 | Appling | A61B 18/24 |
| | | | | 606/7 |
| 2004/0006344 | A1* | 1/2004 | Nguyen | A61M 25/0662 |
| | | | | 606/191 |
| 2005/0085848 | A1* | 4/2005 | Johnson | A61F 2/013 |
| | | | | 606/200 |
| 2006/0020270 | A1* | 1/2006 | Jabba | A61B 17/0057 |
| | | | | 606/139 |
| 2006/0025801 | A1* | 2/2006 | Lulo | A61B 17/1214 |
| | | | | 606/200 |
| 2006/0100602 | A1* | 5/2006 | Klint | A61B 17/12113 |
| | | | | 604/524 |
| 2006/0116709 | A1* | 6/2006 | Sepetka | A61B 17/12145 |
| | | | | 606/200 |
| 2007/0083257 | A1 | 4/2007 | Pal et al. | |
| 2007/0293887 | A1* | 12/2007 | Okushi | A61M 25/10 |
| | | | | 606/200 |
| 2008/0172087 | A1* | 7/2008 | Fuchs | A61B 17/115 |
| | | | | 606/213 |
| 2009/0157052 | A1 | 6/2009 | Verbitsky et al. | |
| 2011/0282447 | A1* | 11/2011 | Niu | A61F 2/0805 |
| | | | | 623/13.11 |
| 2012/0265237 | A1* | 10/2012 | Evert | A61B 17/12145 |
| | | | | 606/200 |
| 2014/0171988 | A1* | 6/2014 | Noriega | A61B 17/3421 |
| | | | | 606/159 |
| 2014/0257363 | A1 | 9/2014 | Lippert | |
| 2014/0277097 | A1 | 9/2014 | Castleberry et al. | |
| 2014/0324096 | A1 | 10/2014 | Ngo et al. | |
| 2016/0022271 | A1* | 1/2016 | Ferry | A61B 17/1215 |
| | | | | 606/200 |

OTHER PUBLICATIONS

PCT, International Search Report and Written Opinion from App No. PCT/US2016/048715, dated Oct. 31, 2016, 16 pages.

* cited by examiner

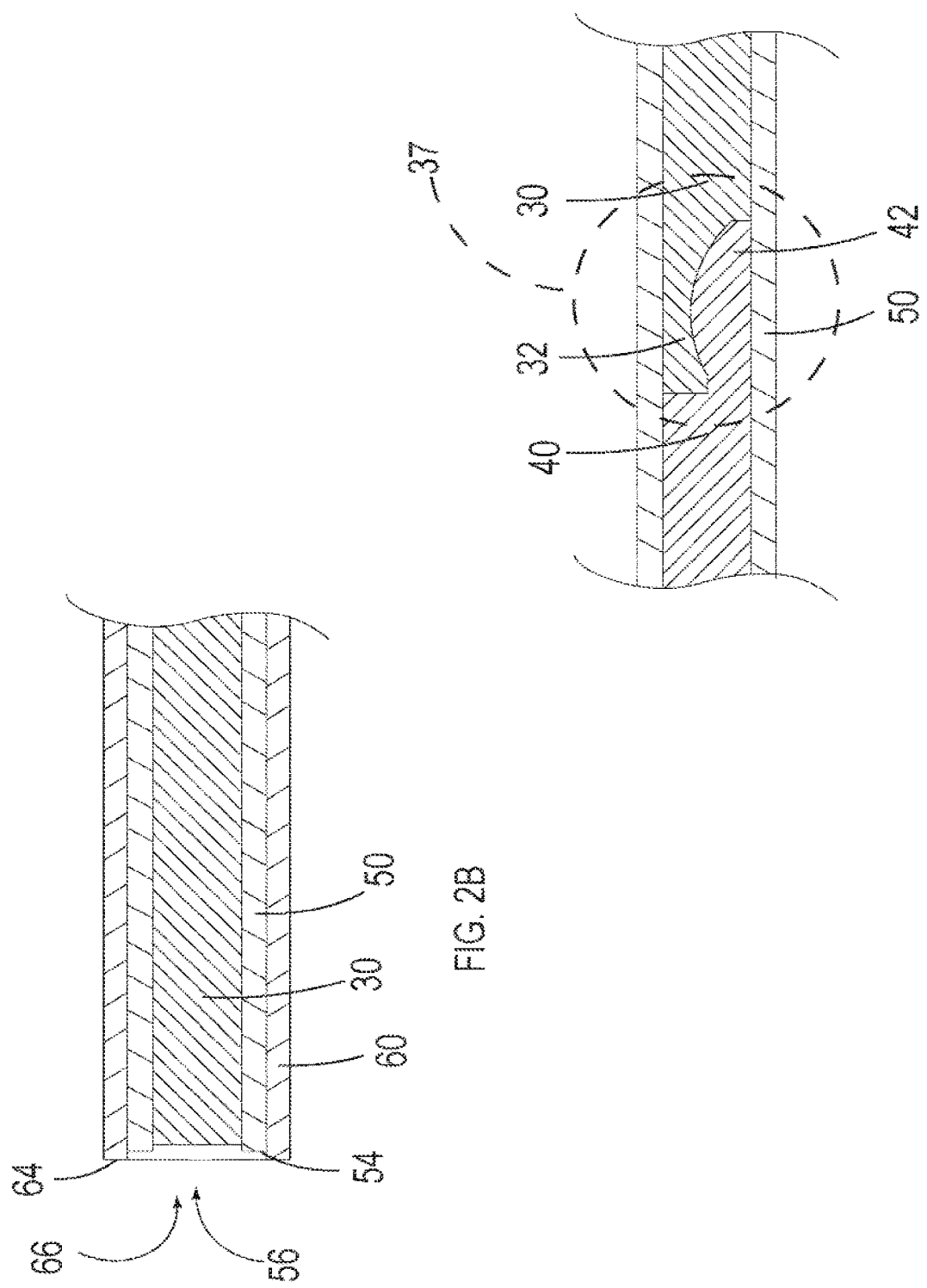

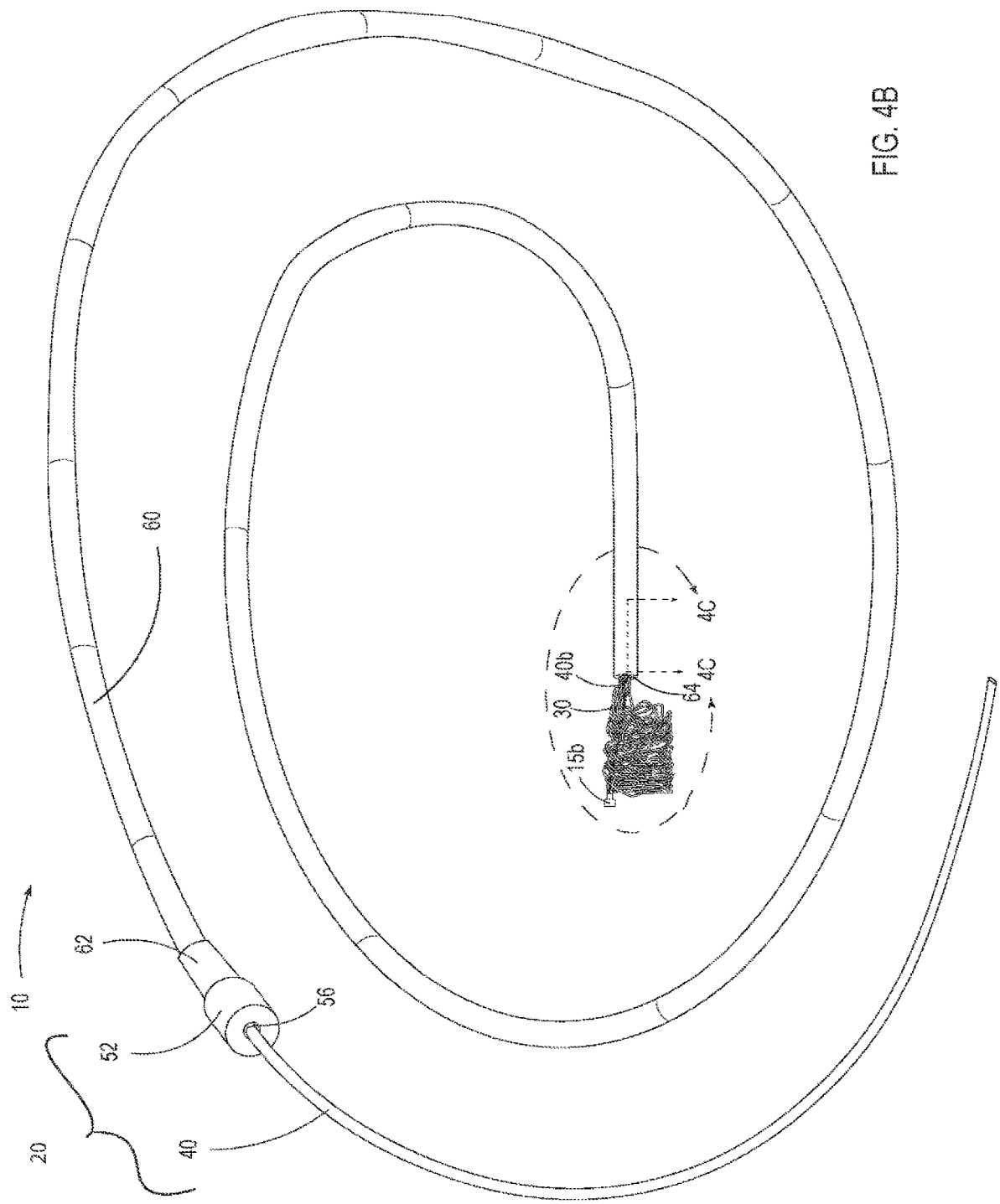

SLEEVE FOR DELIVERY OF EMBOLIC COIL

CROSS REFERENCE TO RELATED APPLICATIONS

This application claims the benefit of priority of U.S. provisional application No. 62/209,736 filed 25 Aug. 2015 entitled "Sleeve for delivery of embolic coil," which is hereby incorporated herein by reference in its entirety for the purposes of PCT Rules 4.18 and 20.6.

TECHNICAL FIELD

The disclosure herein relates generally to medical devices used with intravascular catheters. More particularly, it relates to a sleeve that contains embolic devices for delivery through the catheters.

BACKGROUND

Intravascular catheters are common medical devices that are manufactured by numerous companies. The various companies provide catheters that have different physical performance attributes that physicians find attractive for the purposes of accessing a targeted vessel in the highly tortuous/varied vascular anatomy of each patient. The various catheters are provided in numerous length options and are provided with numerous pre-curved tip shapes and mechanical structure (e.g., bending stiffness/softness and "torqueability" to orient the tip shape remotely). Additionally, catheters are provided with variations in their internal lumen in both diameter size and surface material. In some medical procedures, the vascular catheter is routinely used to deliver embolic devices such as endovascular embolization coils to a particular target location in the vasculature to conduct vascular occlusions or embolizations to stop the blood flow in a vessel or isolate a vascular area from blood flow.

The various differences in physical attributes of the catheters, for example, relative roughness or friction coefficient of the material forming the interior surface, impacts the potential compatibility of using certain catheters with different manufacturers' embolic devices. For example, Boston Scientific contraindicates the use of its Interlock embolic coil products with any polyurethane, soft-tip catheter, for example, Terumo Glide catheters or AngioDynamics Soft-Vu catheters. These limitations detrimentally impact the ability of the embolic coil manufacturer to gain clinical use of their coil when the physician wants to use one of these catheters due to the feature benefits of the catheter in accessing the target vessel. In some instances, the physician may be forced to "exchange" one catheter for another over the guidewire to achieve a compatible catheter for deployment of the embolic device, which is a costly and inefficient method.

With current technology, embolic devices (such as coils) use an introducer tube to advance the coil into the catheter. The function of the introducer tube is to hold the device straight (i.e., in an uncoiled form) outside of the catheter and facilitate "introducing" the device into the catheter. In this structure, the embilic device is fed directly into the catheter, necessitating compatibility between the embolic device and the catheter, e.g., compatibility between outer diameter of the embolic device and inner diameter and surface of the catheter lumen and material compatibility between the material forming the embolic device and the catheter material to ensure smooth advancement of the embolic device through the catheter lumen. Thus, cost is increased and physician alternatives are reduced.

Clinicians utilize various imaging modalities such as fluoroscopy to direct the embolic device to the end of the catheter and into the targeted area for treatment. However, this reliance on the imaging modalities while the embolic device travels through the catheter requires additional cost and time, which results in heightened risk to the patient. As such, these risks and costs represent the insufficiency of typical solutions and room for improvements in the industry.

The information included in this Background section of the specification, including any references cited herein and any description or discussion thereof, is included for technical reference purposes only and is not to be regarded subject matter by which the scope of the invention is to be bound.

SUMMARY

In order to address the shortcomings of the status quo, the following disclosure presents device that may be used in conjunction with catheters to aid in the delivery of a therapeutic device, e.g., one or more embolic coils, through a catheter which might otherwise be contraindicated for such delivery due to an incompatibility as discussed above. The device may take the form of a sleeve made, in part, of a material having a low coefficient of friction in which the device is housed or otherwise retained until delivery. The sleeve may provide a more appropriate environment for delivery of the therapeutic device than the lumen of the catheter. For example, the delivery sleeve may provide a lower friction interface with the therapeutic device allowing the therapeutic device to easily slide as it is pushed through the sleeve to the end of the deliver catheter instead of possibly getting caught on or damaged by the wall of the delivery catheter. The delivery sleeve may further provide structural support, radial compressive or resistive force along the length of the therapeutic device, thereby providing longitudinal strength and support to the therapy device such that it can be advanced along the catheter 60 without bucking, kinking, or crushing.

In one implementation, an endovascular apparatus includes a delivery sleeve, a therapeutic device, an advancement mechanism, and a stop. The delivery sleeve has a longitudinal lumen extending between a proximal end and a distal end. The therapeutic device may be housed within and extend substantially an entire length of the delivery sleeve. The advancement mechanism may be configured to engage the therapy device to advance the therapy device into a patient. A stop may be positioned on the proximal end of the delivery sleeve and is operable to limit a distance the delivery sleeve is inserted into a catheter. An outside diameter of the delivery sleeve is sufficiently small such that the delivery sleeve may be inserted into a catheter and a diameter of the lumen is sufficiently large such that the lumen is able to coaxially receive the therapeutic device and the advancement mechanism therein but sufficiently small that the delivery sleeve adds longitudinal strength to the therapeutic device.

In another implementation, an endovascular system includes a catheter, a delivery sleeve, a therapy device, an advancement mechanism, and a stop. The catheter may have a proximal catheter end and a distal catheter end with a longitudinal catheter lumen extending therebetween. The delivery sleeve may have a proximal end and a distal end with a longitudinal lumen extending therebetween. The delivery sleeve may be coaxial with and movable within the catheter lumen. The therapeutic device may extend substantially an entire length of the delivery sleeve, or even slightly beyond the distal length, and may be located coaxially within the lumen of the delivery sleeve and movable therein. The advancement mechanism may be connected to the therapy device and configured to advance the therapy device into a patient. The stop may be positioned on the proximal end of the delivery sleeve which contacts the proximal end of the catheter to limit the distance the delivery sleeve is inserted into a catheter. The stop may be part of a deployment handle that controls advancing the therapy device into a patient.

In a further implementation, a method for delivering a therapeutic treatment to a patient is disclosed. A catheter may be provided having a proximal catheter end and a distal catheter end with a longitudinal catheter lumen extending therebetween. A therapeutic delivery device apparatus may be provided including a delivery sleeve, a therapeutic device, an advancement mechanism, and a stop. The delivery sleeve may have a proximal end and a distal end with a longitudinal lumen extending therebetween. The delivery sleeve may be coaxial with and longitudinally movable within the catheter lumen. The therapeutic device may extend substantially an entire length of the delivery sleeve, or even slightly beyond the distal end, and may be enclosed coaxially within the lumen of the delivery sleeve and longitudinally movable therein. The advancement mechanism may be connected to the therapeutic device and configured to advance the therapy delivery device into a patient. The stop may be positioned on the proximal end of the delivery sleeve which contacts the proximal catheter end of the catheter, limiting a distance the delivery sleeve is inserted into the catheter. The method may further include inserting the therapeutic delivery device into the catheter until the stop comes into contact with the proximal end of the catheter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments and implementations and illustrated in the accompanying drawings.

BRIEF DESCRIPTION OF THE DRAWINGS

FIG. 2B illustrates a detailed cross-section view of the endovascular system of FIG. 2A taken along section 2B-2B.

FIG. 3B illustrates a detailed cross-section view of the endovascular system of FIG. 3A taken along section 3B-3B.

FIG. 4B illustrates a perspective view of an endovascular system with a plurality of parallel embolic coils in accordance with various embodiments.

DETAILED DESCRIPTION

Various embodiments related to systems and methods for treating patients via intravascular catheters are disclosed herein. However, in contrast to traditional catheter configurations, a temporary, disposable sleeve may be used to separate the catheter from the particular therapy device being delivered through the catheter. The sleeve may minimize the effects of the inner lumen characteristics of different catheter materials, geometries, and construction on devices or instruments passed through the catheter to provide the desired therapy. The sleeve may reduce variability between different catheter designs and provide a stable, regular lumen of known physical and performance characteristics. This may enable development of therapeutic products without the limitation and complexity of having to design for use with all catheters and minimizes the limitations of indicating (or contra-indicating) specific catheters for use. Such devices or instruments may include embolic devices and, in particular, examples may be embolic coils for administering a vascular embolization or occlusion.

The sleeve may be formed from a flexible tube made up of a bio-compatible material or constructed of multiple layers of biocompatible materials. The sleeve may have a thin-wall, flexible structure formed of a material operable to slide easily through the lumen of a catheter. The sleeve may have a construction, such as including a wire or fiber braid, that provides mechanical support such as radial or longitudinal rigidity, or both. Similarly, a lumen of the sleeve may be formed of a material that allows a therapeutic device to slide easily along the length of the sleeve. The therapeutic device is loaded into the sleeve ex-vivo, for example, by the manufacturer of the therapeutic device at the time of manufacture. The sleeve may function to hold the therapeutic device in a state for delivery through the catheter, e.g., in a restrained state, that changes to an unrestrained state upon delivery from the sleeve and the catheter in vivo. For example, the sleeve may contain an embolic coil in a stretched, linear form while within the sleeve, which converts to a coil shape upon delivery from the sleeve and catheter. The sleeve with the therapeutic device housed therein may be inserted into and line the inner wall of the catheter. The therapeutic device may then be delivered through a lumen extending along the longitudinal length of the sleeve.

Figure 1:
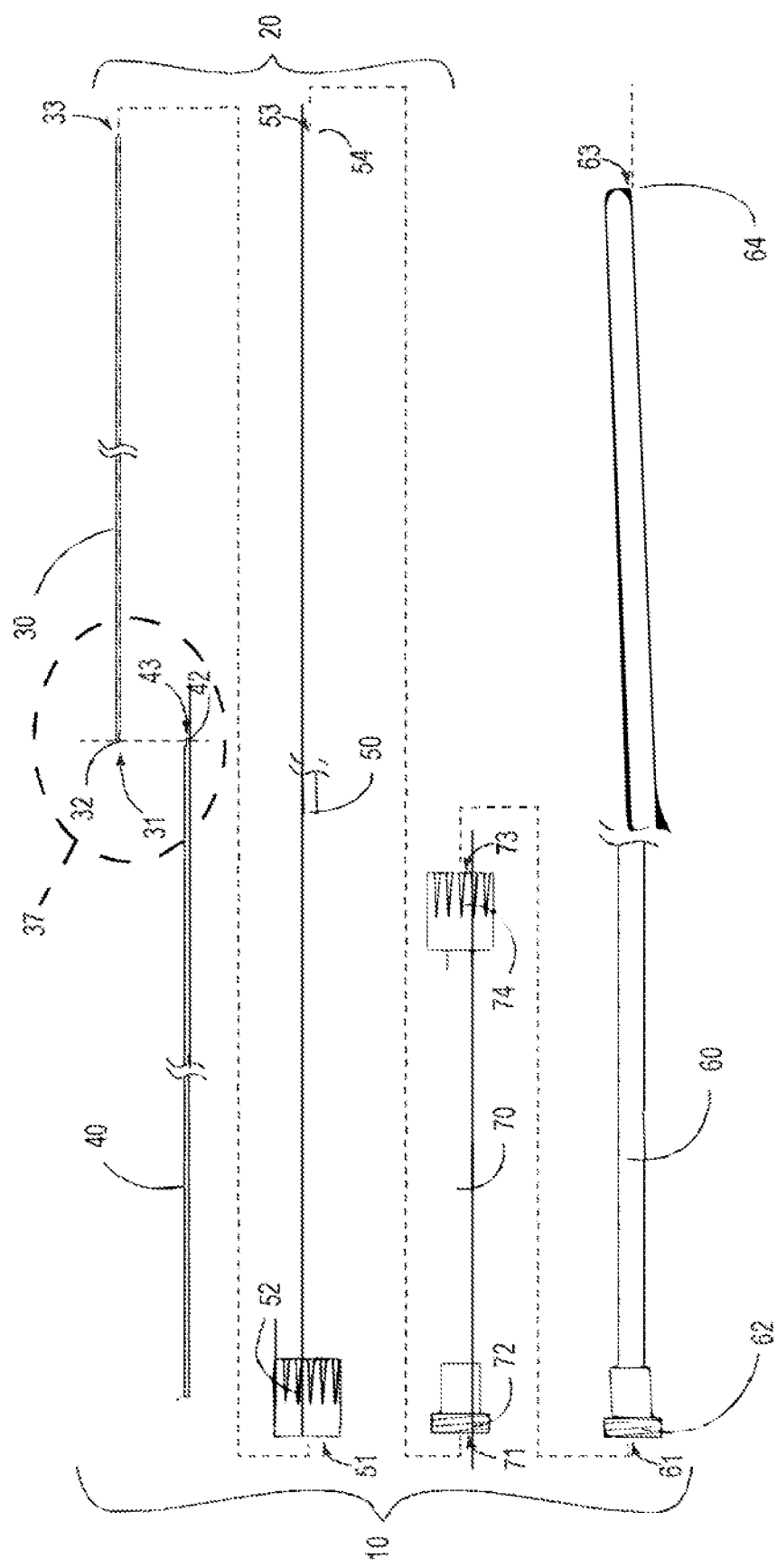
FIG. 1 illustrates an exploded view of an endovascular system in accordance with various embodiments.

As shown in the exploded view of FIG. 1, an exemplary endovascular system 10 may include a therapy delivery device 20 and a catheter 60. The therapy delivery device 20 may include a therapy device 30. The therapy device 30 may be connected to an advancement device 40 via a connection mechanism 37. The therapy device 30 may be insertable and movably positioned within a delivery sleeve 50. The therapy delivery device 20 may be movably positioned within the catheter 60. The delivery sleeve 50 may be connected to the catheter 60. The endovascular system 10 may include an extension 70 that is positioned on a proximal end of the catheter 60 to accommodate a delivery sleeve 50 that is longer in length than the catheter 60.

The catheter 60 may be any type of intravascular catheter known in the industry suitable to be placed in the body of a patient. For example, the catheter 60 may include a single lumen 66 (see FIG. 2B) or the catheter 60 might include multiple lumens (not shown). The catheter 60 may be operable to follow a tortuous path to reach a target site. The catheter 60 may have a first distal end 63 with respect to the user. The distal end 63 may include an outlet 64 operable to deliver the therapy device 30 near the target therapy site within the patient. The catheter 60 may have a proximal end 61 with respect to the user. The proximal end 61 may include an attachment mechanism 62. The attachment mechanism 62 may be in the form of a luer fitting operable to connect with other medical devices.

As indicated above, the therapy delivery device 20 may include the therapy device 30 and a delivery sleeve 50. The delivery sleeve 50 is a component that may be used in conjunction with the therapy device 30. The delivery sleeve 50 may include a single lumen 56 (see FIG. 3B) extending between a distal end 53 and a proximal end 51. The delivery sleeve 50 may be sufficiently flexible to follow the lumen 66 of the catheter 60. The distal end 53 of the delivery sleeve 50 may include an outlet 54 configured to be positioned near the distal end 63 of the catheter 60 adjacent to the target therapy site and allow the therapy device 30 to exit both the outlet 54 of the delivery sleeve 50 and the outlet 64 of the catheter 60 proximal to the target therapy site within the patient.

Figure 2A:
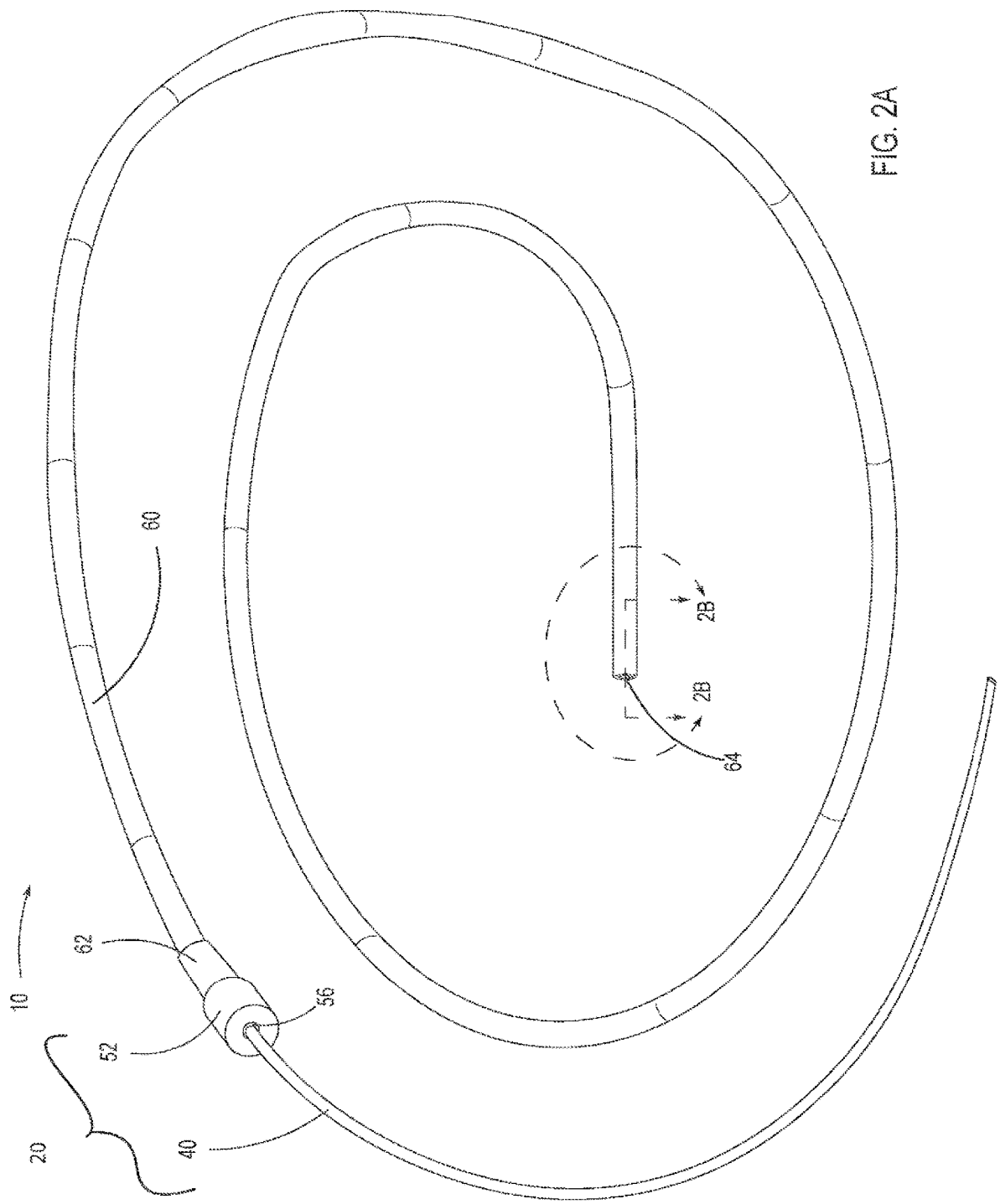
FIG. 2A illustrates a perspective view of an endovascular system in accordance with various embodiments.

The proximal end 51 of the delivery sleeve 50 may include a stop 52 that is positioned to limit the travel of the delivery sleeve 50 into the lumen 66 of the catheter 60. In some embodiments, the stop 52 may be an attachment mechanism suitable to connect to the proximal end 61 of the catheter 60. In one example, the attachment mechanism of the stop 52 may be a luer fitting operable to connect with the luer fitting attachment mechanism 62 on the catheter 60 or operable to connect to other medical devices. As shown in FIG. 2A, the therapy delivery device 20 may be positioned within the catheter 60 (the advancement device and the sleeve cap are the portions of the delivery device 20 shown in FIG. 2A.) The positioning may be coaxial. In this configuration, the delivery sleeve 50 may extend through the lumen 66 of the catheter 60.

The delivery sleeve 50 may be made of a flexible, low-friction material suitable to glide easily through the lumen 66 of the catheter 60. The low-friction material may be, for example, a bio-compatible material such as a polytetrafluoroethylene (PTFE) material formed as a tube defining the lumen 56. The material is not limited to PTFE, but may include any other bio-compatible materials with sufficient lubricity such as other fluoropolymers or modified polymers having a lubrication agent or lubricating coatings. For the purposes of this disclosure, materials with a low coefficient of friction suitable for forming, lining, or coating the lumen of the delivery sleeve 50 may have a coefficient of friction ≤0.1. In various embodiments, the material provides a lubricious surface on both the outside and inside of the delivery sleeve 50. The outside surface of the delivery sleeve 50 interacts with the interior lumen 66 of the catheter 60 during deployment of the delivery sleeve 50. The inside surface defining the lumen 56 of the delivery sleeve 50 interacts with the exterior of the therapy device 30. In one exemplary embodiment, the delivery sleeve 50 may be an unreinforced, natural, single-wall PTFE tube. In another exemplary embodiment, the delivery sleeve 50 may be a reinforced, composite structure incorporating a PTFE inner lumen, a stainless steel wire braid, and a polyimide outer jacket.

In some exemplary embodiments, the inner and outer surfaces of the delivery device 50 may be made of different material to optimize the interaction with the opposing surface (catheter 60 or therapy device 30). The thickness of the wall of the delivery sleeve 50 may be from about 0.001 to about 0.01 inches (about 0.025 mm to about 0.25 mm) thick. More particularly, the wall of the delivery sleeve 50 may be about 0.002 inches (about 0.05 mm) thick. The wall of the delivery sleeve 50 may be sufficiently fluid tight to allow fluid flushing through the length of the delivery sleeve 50. The material forming the delivery sleeve 50 may be made kink resistant, including by reinforcing the tubing utilizing coils, braids, spirals, fibers, or composite materials such as co-polymers. Other materials may be used as reinforcement of the wall of the delivery sleeve 50 as well including metallic ones. While the delivery sleeve 50 is sufficient flexible for endovascular travel, it is also sufficiently strong such that is can be advanced through the catheter 60 as a column.

The delivery sleeve 50 may be manufactured in a number of diameters depending on the vascular application. In one example, the delivery sleeve 50 may have about a 0.04 inch (about 1.02 mm) outside diameter and about a 0.036 inch (about 0.91 mm) inside diameter resulting in a wall thickness of about 0.002 inch (0.0508 mm). Such sizes may provide suitable compatibility with 4 French to 5 French catheter applications. In various other examples, the sleeve may include about 0.035-0.038 inch (about 0.09 mm-0.1 mm) inside diameters and/or 0.039-0.042 inch (about 0.1 mm-0.11 mm) outside diameters. While these various examples may be used, it may be preferable to size the delivery sleeve 35 according to the preferred catheter/therapy device combination.

The inside diameter of the delivery sleeve 50 may also be sized to add longitudinal compressive strength to the therapy device 30 such that it can be advanced along the catheter 60 easier without kinking or crushing. The delivery sleeve 50 may provide a homogeneous and consistent surface for delivery of the therapy device 30 through the catheter. In contrast, the inner surface of the catheter varies from catheter to catheter and manufacturer to manufacturer.

As noted above, the therapy delivery device 20 may include an advancement mechanism 40 that connects to the therapy device 30 to push the therapy device 30 through the lumen 56 of the delivery sleeve 50. The therapy device 30 may be coupled with the advancement mechanism 40 by a connection system 37. The connection system 37 may comprise any of a number of known systems with opposing features 32, 42 that interconnect a therapy device 30 to an advancement mechanism 40 (e.g., an embolic coil device to a pusher wire). The internal diameter of the lumen 56 of the delivery sleeve 50 may be sized to assist in maintaining engagement between the opposing features 32, 42 of the connection system 37 by providing a consistent cross-sectional area within and along the lumen 56 of the delivery sleeve 50. The diameter of the lumen 56 of the delivery sleeve 50 may thus be optimized to maintain sufficient pressure on the connection system 37 to limit premature release. The delivery sleeve 50 thus provides an advantage, which is not provided by the various catheters on the market.

The delivery sleeve 50 may extend through the catheter lumen 66 until the stop 52 engages with the proximal end 61 of the catheter 60. This engagement may be configured to position the distal end 51 of the delivery sleeve 50 at a desired location within the catheter 60. For example, in some embodiments, the delivery sleeve 50 may have a length that extends approximately to the distal end 63 of the catheter 60 when the stop 52 engages the proximal end 61 of the catheter 60. As shown in FIG. 2B, the distal end 53 of the delivery sleeve 50 may extend approximately the same distance as the distal end 63 of the catheter 60. Any difference in length may be nominal such as caused by a difference in tolerances of the two devices or use of catheter or therapeutic device accessories.

The distal end 33 of the therapy device 30 may likewise extend to the distal end 53 of the delivery sleeve 50. Preferably, the distal end 33 of the therapy device 30 is adjacent and proximal to the distal end 53 of the delivery sleeve 50, which extends to a point immediately proximal to the distal end 63 of the catheter 60. In some exemplary embodiments, the length of the therapy device 30 may be coextensive with the length of the delivery sleeve 50. In various exemplary embodiments, the stop 52, which limits the distance that the distal end 53 of the delivery sleeve 50 extends within the catheter 60, may be a female luer fitting 5. The stop 52 may removably connect to the attachment mechanism 62, which may be a male luer fitting. The distal end 53 of the delivery sleeve 50 may extend from the stop 52 approximately to the distal end 63 of the catheter 60. By sizing the delivery sleeve 50 in accordance with the catheter 60 such that the distal ends 53, 63 extend to approximately the same length, the delivery sleeve 50 may be inserted into the catheter 60 and extended to the distal end 63 without the use of an imaging modality such as fluoroscopy to determine its location. For example, a 100 cm delivery sleeve length would be designed for use with a 100 cm catheter length, enabling the precise placement of the distal end 53 of the delivery sleeve 50 without need for using an imaging modality.

In accordance with another exemplary embodiment, the delivery sleeve 50 may be longer than the catheter 60. In such an embodiment, the precise placement of the distal end 53 of the delivery sleeve 50 relative to the distal end 63 of the catheter may still be accomplished by pairing the delivery sleeve 50 with an extender 70. If a user desired to use a catheter 60 that is shorter than the length of the delivery sleeve 50, when the stop 52 on the delivery sleeve 50 abuts the attachment mechanism 62 on the proximal end 61 of the catheter 60, the distal end 53 of the delivery sleeve 50 would extend outward beyond the distal end 63 of the catheter 60 and into the patient. Such a situation could increase the procedural risk of damaging a vessel, thereby harming the patient and require that the clinician use fluoroscopy to navigate the distal end 53 of the delivery sleeve 50 through the length of the catheter 60 to ensure that it does not enter into the vessel, thus increasing the time needed to perform the procedure.

However, it is possible for the longer delivery sleeve 50 to be used with a desired shorter catheter by using the extender 70. The extender 70 may include a distal end 73 with respect to the user and a proximal end 71 with respect to the user. Each end of the extender 70 may have an attachment mechanism 72, 74 such as a luer fitting. In various embodiments the attachment mechanism 72 at the proximal end 71 may be a male luer as shown and the attachment mechanism 74 at the distal end 73 may be a female luer fitting (although each end may use ether type of fitting, male or female as long as the opposing fitting mates). The extender 70 defines a lumen extending between the proximal end 71 and the distal end 73 that is sized similarly or the same as the lumen 66 of the catheter 60. The extender 70 may have a length that is about equal to the length that the delivery sleeve 50 extends beyond the catheter 60 in response to the delivery sleeve stop 52 (e.g., a luer fitting) engaging the proximal end 61 of the catheter 60.

It should be appreciated that when using the extender 70, the delivery sleeve stop 52 does not directly engage the proximal end 61 of the catheter 60. Instead, the delivery sleeve stop 52 may engage the proximal end 71 of the extender 70. For example, the stop 52 in the form of a luer fitting may engage the attachment mechanism 72 (e.g., and opposing luer fitting) with the delivery sleeve 50 extending through the extender 70 lumen. The distal end 73 of the extender 70 may then be connected to the proximal end 61 of the catheter 60. The distal attachment mechanism 74 of the extender 70 may connect to the attachment mechanism 62 at the proximal end 61 of the catheter 60.

For example, if the user desires to use a shorter catheter 60 (e.g., a 65 cm catheter) with a longer delivery sleeve 50 (e.g., a 100 cm delivery sleeve), then the delivery sleeve 50 will be too long for the catheter 60 without increasing the aforementioned risks. However, by connecting an extender 70 sized to the difference between the catheter length and the delivery sleeve length, the extender 70 takes up the additional length required by the shorter catheter 60 and the longer delivery sleeve 50. Pursuant to this example, the 65 cm catheter can be connected to a 35 cm extender 70, which in combination form a 100 cm delivery device for the delivery sleeve 50 (i.e., 35 cm+65 cm=100 cm). Thus, the extender-catheter combination has a length about the same as the delivery sleeve 50. In this way, the delivery sleeve 50 may be inserted into the extender 70 and further through the attached catheter 60 until the proximal end 61 of the delivery sleeve connects to the proximal end 71 of the extender and the distal end 53 of the delivery sleeve 50 will be located approximately at the distal end 64 of the catheter 60. The location of the distal end 53 of the delivery sleeve 50, and thus the distal end 33 of the therapeutic device 30 contained therein, is positioned adjacent the distal end 63 of the catheter 60 without need for fluoroscopy or other imaging to guide the therapeutic device 30 to that point.

In accordance with various embodiments, multiple different lengths of extenders 70 may be provided with the therapy delivery device 20 to allow compatibility with different length catheters 60. For example, for a 100 cm length delivery sleeve, a 35 cm length extender can be used for 65 cm length catheter compatibility. Alternatively, for a 100 cm length delivery sleeve, a 55 cm length extender can be used for 45 cm length catheter compatibility. Other lengths of extenders 70 can be provided to create similar combinations of extenders 70 and catheters 60 to accommodate the desired use of catheters 60 of various lengths with desired lengths of therapeutic devices 30 housed in delivery sleeves 50.

The extender 70 may be made of a low-friction tubing. The low-friction tube may be formed, for example, of a polytetrafluoroethylene (PTFE) material in the tube structure forming the lumen. The tube may be securely attached to attachment mechanisms 72, 74 at either or both ends. As indicated above, the attachment mechanisms 72, 74 may be luer fittings. However, any suitable connection mechanism, particularly medically suitable mechanisms, may be used. The tubing may be reinforced for better kink-resistance. The extender 70 may have an inside diameter slightly larger than the outside diameter of the delivery sleeve 50 to allow for easy insertion of the delivery sleeve 50 therethrough. The extender 70 may have a wall thickness anywhere from 0.01 mm to 0.10" mm. This diameter and wall thickness may be the same as or larger than the wall thickness of catheter 60 since the extender 70 does not enter the catheter lumen 66. While the extender 70 may be specifically configured to maximize its accommodation of the delivery sleeve 50, the extender 70 may also or alternatively be configured to accommodate specific catheters that a physician may use. In this way, the extender 70 may be formed to match the diameter and structure of the catheter 60 it is used with so there is conformity of parts. Thus, the extender 70 not only provides compatibility with multiple catheter lengths, but also facilitates all procedural, performance, and safety advantages of the delivery sleeve 50.

As indicated above, the therapy delivery device 20 may include the delivery sleeve 50 and a therapeutic device 30. The therapeutic device 30 may include any of a variety of endovascular medical devices. The therapeutic device 30 may be preloaded into the lumen 56 of the delivery sleeve 50 during manufacturing or before the catheterization procedure. In this way, the physician can remove the combination of the delivery sleeve 50 preloaded with the therapeutic device 30 from its packaging and insert the delivery sleeve 50 and therapeutic device 30 combination into the catheter 60 together. The combination may then be advanced along the catheter 60 together until the delivery sleeve 50 hits its stop 52.

Having a delivery sleeve 50 of known length commensurate with the length of the catheter 60 can minimize procedure time by reducing or eliminating fluoroscopic or other angiographic requirements until the therapeutic device 30 is deployed from the outlet 64 of the catheter 60. The delivery sleeve 50, and the therapeutic device 30 positioned therein, can be positioned quickly and accurately because the physician does not need to monitor where the distal end of either the delivery sleeve 50 or the therapeutic device 30 is located until the stop 52 on the delivery sleeve 50 engages the proximal end 61 of the catheter 60. From that point, fluoroscopy (or like technique) may be used to advance only the therapeutic device 30 to the target region.

While the therapeutic device 30 may be any endovascular medical device, as illustrated in FIGS. 1-5, the therapeutic device 30 may be an embolic device configured to form vascular occlusions within a patient. More specifically, the embolic device may be an embolic coil. In accordance with the various embodiments described herein, one or more embolic coils may be delivered through the catheter 60 by advancing the embolic coil(s) (shown in FIGS. 1-5 as therapeutic device 30) and delivery sleeve 50 combination into the catheter 60 until the stop 52 on the delivery sleeve 50 engages the proximal end 61 of the catheter 60. This process positions the embolic coil 30 for deployment into the patient. The embolic coil 30 may extend within the lumen 56 of the delivery sleeve 50 in a restrained form as a linear shape and then take on a complex shape as originally formed after being deployed into the area of interest, such as an aneurysm.

Figure 3A:
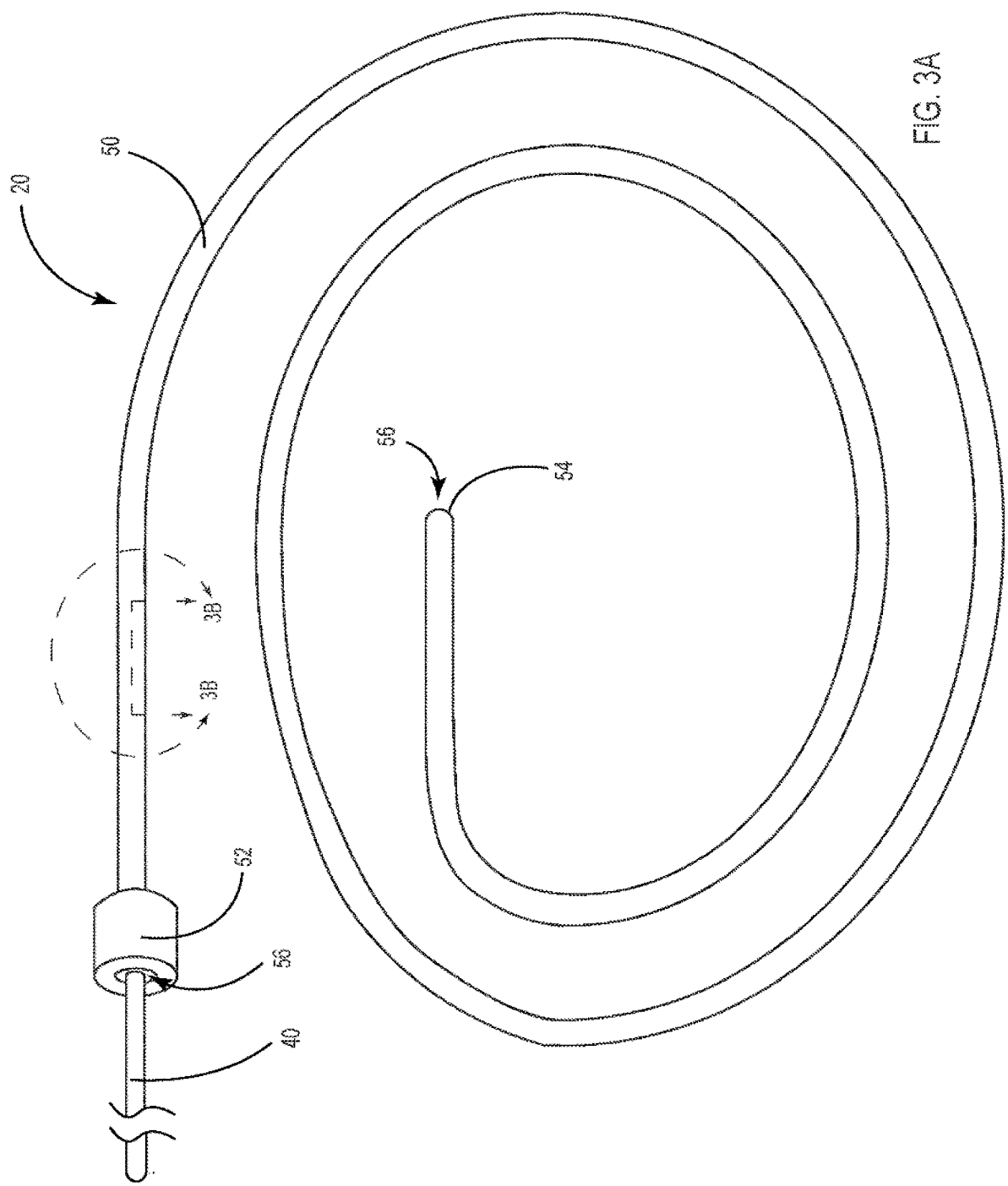
FIG. 3A illustrates a perspective view of a delivery sleeve with a therapeutic device positioned therein in accordance with various embodiments.

The advancement mechanism 40 may be configured to advance the embolic coil 30 via a variety of different ways. The advancement mechanism 40 does not need to rely on a structural interlock. For example, the advancement mechanism 40 may function as an injection device thereby injecting the coil out of the sleeve. In other embodiments, a more structural interface may be incorporated. For example, as shown in FIG. 3B, a connection mechanism 37 may be provided between the embolic coil 30 and the advancement mechanism 40 (shown as a pusher wire). Any connector configuration or coupling mechanism may be used. In the exemplary embodiment of FIG. 3B, the proximal end 31 of the embolic coil 30 may include a receiving feature 32 (such as a recess, slot, aperture, or the like) and is operable to engage a linking feature 42 (such as a protrusion, hook, clasp, or the like) positioned at the distal end of the advancement mechanism 40 used. The receiving feature 32 and the linking feature 42 may be positioned on overlapping tabs that extend from the therapeutic device 30 and the advancement mechanism 40, respectively. The tabs may overlap such that the connection mechanism 37 is not larger than the outside diameters of each of the therapy device 30 and the advancement mechanism 40. To release the therapeutic device 30 from the advancement mechanism 40, the advancement mechanism 40 merely extends the connection mechanism 37 out of the delivery sleeve 50. With the external pressure from the sleeve 50 removed, there is insufficient force to hold the connection mechanism 37 together and the therapeutic device 50 is released from the advancement mechanism 40. As shown in FIG. 2A, the advancement mechanism 40 may be longer than and extend out of the proximal end of the lumen 56 of the delivery sleeve 50.

Ordinarily, using prior art devices and techniques for placement of embolic coils, to complete an occlusion procedure, the physician must sequentially reload the catheter with several additional coils through an introducer that abuts the proximal end of the catheter until it is determined the occlusion is sufficient. This procedure is traditionally performed using typical medical imaging techniques to monitor the position of the embolic coils along the entire length of the catheter. However, by prepackaging one or more embolic coils 30 within a delivery sleeve 50 of known length, the delivery sleeve 50 may be advanced down the catheter 60 until the stop 52 at the proximal end 51 of the delivery sleeve 50 engages the proximal end 61 of the catheter 60 without need for imaging. Further, if additional embolic coils are needed beyond the embolic coil(s) 30 deployed from the initial delivery sleeve 50, the initial delivery sleeve 50 may be removed from the catheter 60 and a new delivery sleeve 50 with additional embolic coils 30 may be inserted into and advanced down the catheter 60 without need for angiography. This procedure makes the transition between additional embolic coils much quicker, cheaper, and safer.

Figure 4A:
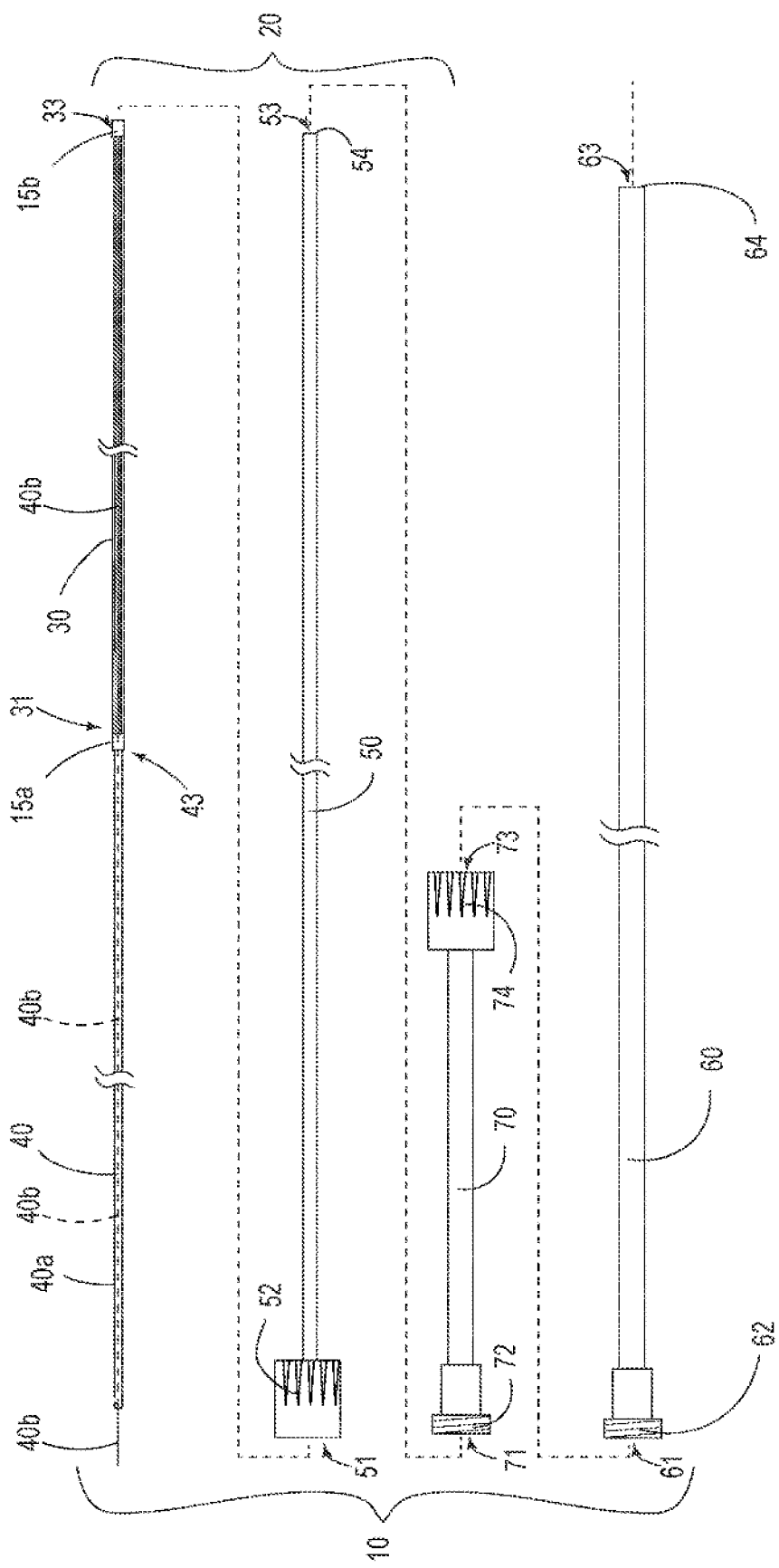
FIG. 4A illustrates an exploded view of an endovascular system with a plurality of parallel embolic coils in accordance with various embodiments.
Figure 4C:
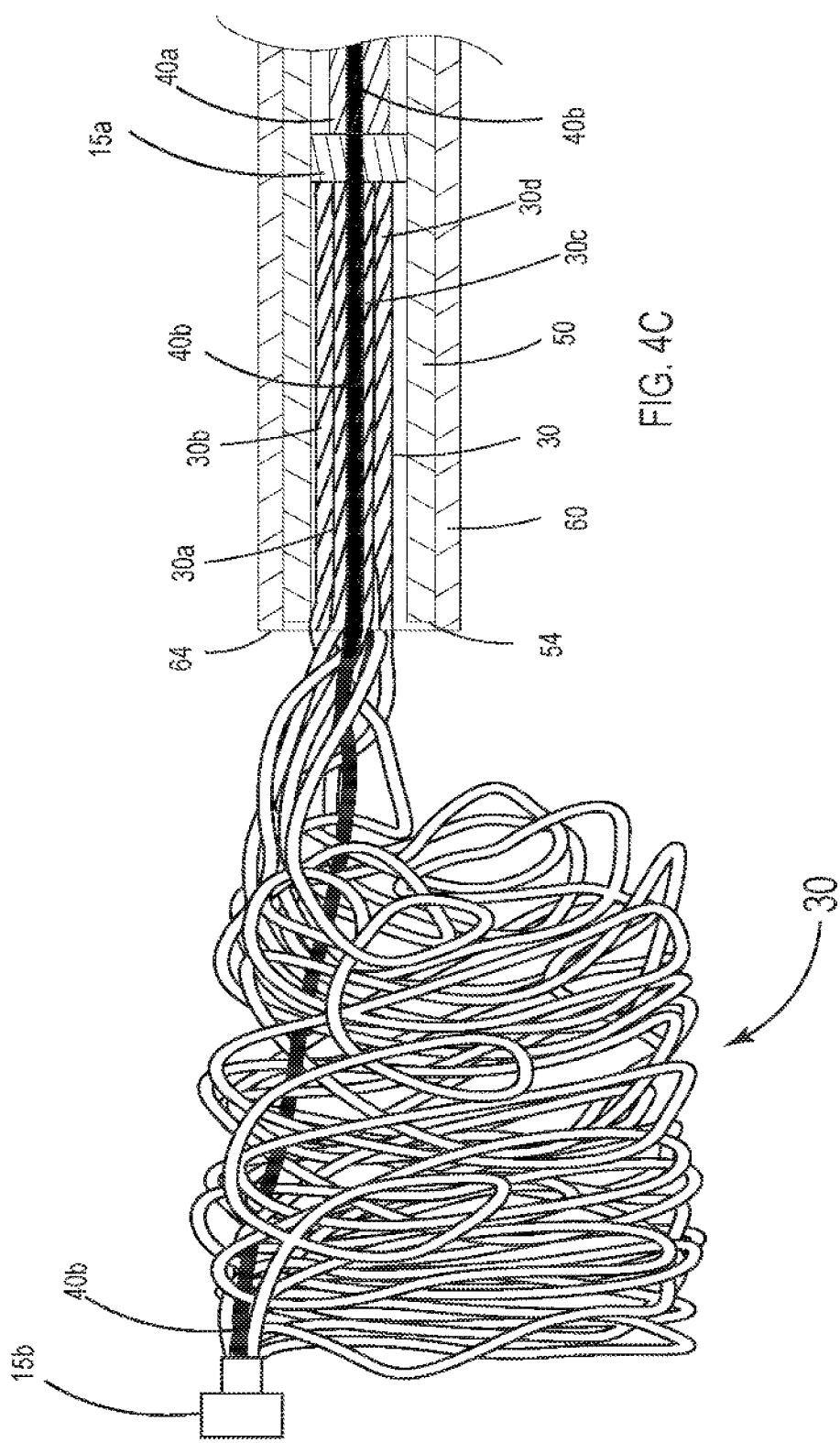
FIG. 4C illustrates a detailed cross-section view of the endovascular system of FIG. 4B taken along section 4C-4C.

There are many known variations of embolic coils, including many different types of metallic and polymer coils. Various coils are made from different materials and are designed with different means of controlling various characteristics such as enhancing thrombogenic response. Coils may be formed as a singular coil or the coils may comprise multiple coil devices packaged together and stored inside the sleeve together. By way of Example, FIGS. 4A-4C illustrate an endovascular system with a plurality of parallel embolic coils in accordance with various embodiments. FIG. 4A shows the endovascular system 10 in an exploded view. Similar to other embodiments discussed herein, this endovascular system 10 may include an advancement mechanism 40 and the therapeutic device 30. This therapeutic device 30 in such an embodiment includes a plurality of embolic coils. The plurality of embolic coils can be inserted into the delivery sleeve 50, which in turn is insertable into and through the catheter 60. The plurality of embolic coils can then be delivered from the distal end 64 of the catheter as illustrated in FIG. 4B. As illustrated in the detailed cross section of FIG. 4C, the plurality of coils forming the therapeutic device remains organized within the delivery sleeve 50 until dispensed from the end.

In accordance with various embodiments, as illustrated in FIG. 4C the plurality of coils may include separate coils 30a, 30b, 30c, and 30d. As illustrated in FIGS. 4A-4C, the coils may be bound on each end by retaining feature 15a, 15b. The advancement mechanism may include one or more separate members. For example, as shown in FIGS. 4A-4C, an inner advancement member 40b may extend the distal retaining feature 15b. An outer advancement member 40a may extend the proximal retaining feature 15a. Each of the separate coils 30a, 30b, 30c, and 30d, the proximal advancement feature 15a, the distal advancement feature 15b, inner advancement member 40b and outer advancement member 40a may all be contained within the delivery sleeve 50. The outer and inner advancement members 40a, 40b and related proximal and distal retaining features 15a, 15b may be configured as any of the types of pusher systems providing both proximal and distal control of delivery of the therapeutic device 30 as disclosed and described in U.S. Patent Application Publication No. US20140039542A1, which is hereby incorporated by reference herein in its entirety. Further, such pusher systems with proximal and distal control can be used to deliver a therapeutic device 30 such as an embolic coil composed of only a single length of coil within the delivery sleeve 50 rather than a plurality of separate coils delivered in parallel as depicted in this example.

The various embodiments and examples disclosed herein may be used with any of the known embolic coils and coils of similar purpose. Each and every therapeutic device, however, will not be discussed herein, but exemplary processes, devices, embodiments are known, and examples of some of these devices include embolic coils that may be used with embodiments of the delivery sleeve disclosed herein, which are described in U.S. Patent Application Publication No. 2012/0046687, U.S. Patent Application Publication No. US20130085518A1, Patent Cooperation Treaty international application Publication No. WO/2013/109784, and Patent Cooperation Treaty international application Publication No. WO/2014/160320. Each of these publications is hereby incorporated by reference in its entirety. Each of the various types of embolic devices described therein may be used with the delivery sleeve disclosed herein.

For the purpose of further description herein, examples will be directed to detachable embolic coils, i.e., embolic coils that can be advanced or retracted by an advancement mechanism (e.g., a pusher wire) until the embolic coil exits the catheter. In some exemplary implementations, a number of embolic coils may be attached to each other end to end within the delivery sleeve 50 with the proximal end of the proximal embolic coil attached to the pusher wire. More particularly detachable polymer coils (DPC) are discussed herein as an example of the therapeutic device 30, but, as indicated, this is not limiting as a person of ordinary skill in the art may apply the concepts provided herein to other types of coils in addition to those incorporated by reference.

In accordance with various embodiments, the therapeutic device 30 may be a single, long detachable polymer coil (DPC) or a series of shorter DPCs attached to each other within the delivery sleeve 50. The DPC may have a lubricious surface to aid in travel through the tighter fit of the delivery sleeve 50 as opposed to traveling through the much larger catheter lumen 66.

In one exemplary implementation, the proximal end 31 of the embolic coil 30 may have a connection mechanism 32 and the distal end 33 may be configured to engage the targeted treatment area to begin creating the occlusion structure. The embolic coil 30 may have a length commensurate with the length of the sleeve 50. To provide more material at the treatment area, longer coil lengths may be desirable (e.g., longer than 100 cm). To accommodate this, longer delivery sleeve lengths may be used such that the entire length of the embolic coil 30 along with the connection mechanism 37 and a portion of the advancement mechanism 40 is contained within the lumen 56 of the delivery sleeve 50.

As indicated above, appropriate lengths of extenders 70 can also be incorporated into the system so that embolic coil lengths can be increased. Longer embolic coils 30 may be retained within commensurately longer sleeves 50. However, physicians are still able to use desired catheters 60 of shorter lengths by using extenders 70 of appropriate lengths in conjunction with the shorter catheters 60. For example, if a 200 cm DPC coil is desired, accordingly it would be provided in a 200 cm length delivery sleeve 50. If the longest catheter length used will be 100 cm, then the luer attachment mechanism 62 of the catheter 60 would be around the midpoint length of the delivery sleeve 50 (i.e., at about 100 cm). This delivery sleeve 50 configuration would be undesirable with the 100 cm catheter length, but with an extender of 100 cm the system would be modified to thereby match the sleeve 50 length of 200 cm with the combination length of catheter 60 at 100 cm and the extension tube at 100 cm. Alternatively, if the user wanted to use a 65 cm catheter length, then a longer extender 70 of 135 cm would need to be attached to the delivery sleeve 50 to provide compatibility with the shorter catheter. The delivery sleeve length is preferably as long as (or longer than) the longest coil 30. When these factors are known, then the appropriate extension tube lengths can be calculated and provided.

The endovascular system 10 may include accessories operable to provide additional therapeutic benefits to the patient. For example, the endovascular system 10 may include medical device accessories that allow sending a flushing fluid or liquid therapy treatment (e.g., saline or medication) through the catheter in conjunction with the therapy device 40. Such flushing devices could include dual port luer access attachment mechanisms. The delivery sleeve 50 may also be configured for use with a flushing system. For example, the wall of the delivery sleeve 50 may be perforated to allow flushing solution to pass through the delivery sleeve 50 such that fluid may be introduced into the delivery sleeve 50 but also reach and flush the catheter 60. It may be noted, that the addition of a medical device accessory like the dual port luer access may cause a length change to the catheter or sleeve. The difference in length may be considered minimal as discussed above or the difference length could be significant warranting the use of the extender 70 discussed above.

In accordance with the various embodiments discussed herein, the delivery sleeve 50 may improve the treatment of a patient because the user can advance the delivery sleeve 50 into the catheter lumen 66 without using fluoroscopy, as the length of the delivery sleeve 50 may be sized relative to the length of the catheter. Additionally, the delivery sleeve 50 may be secured to the catheter 60, increasing the stability of the system with the delivery sleeve 50 positioned inside the catheter 60, particularly during advancement of the therapy device 30, such as situations in which the therapy device 30 is an embolic coil system. Also, by connecting the delivery sleeve 50 to the catheter 60, continuous flush can be maintained through both the delivery sleeve 50 and the catheter 60, reducing delivery friction of the therapy device 30 within the delivery sleeve 50 and catheter 60.

Figure 5:
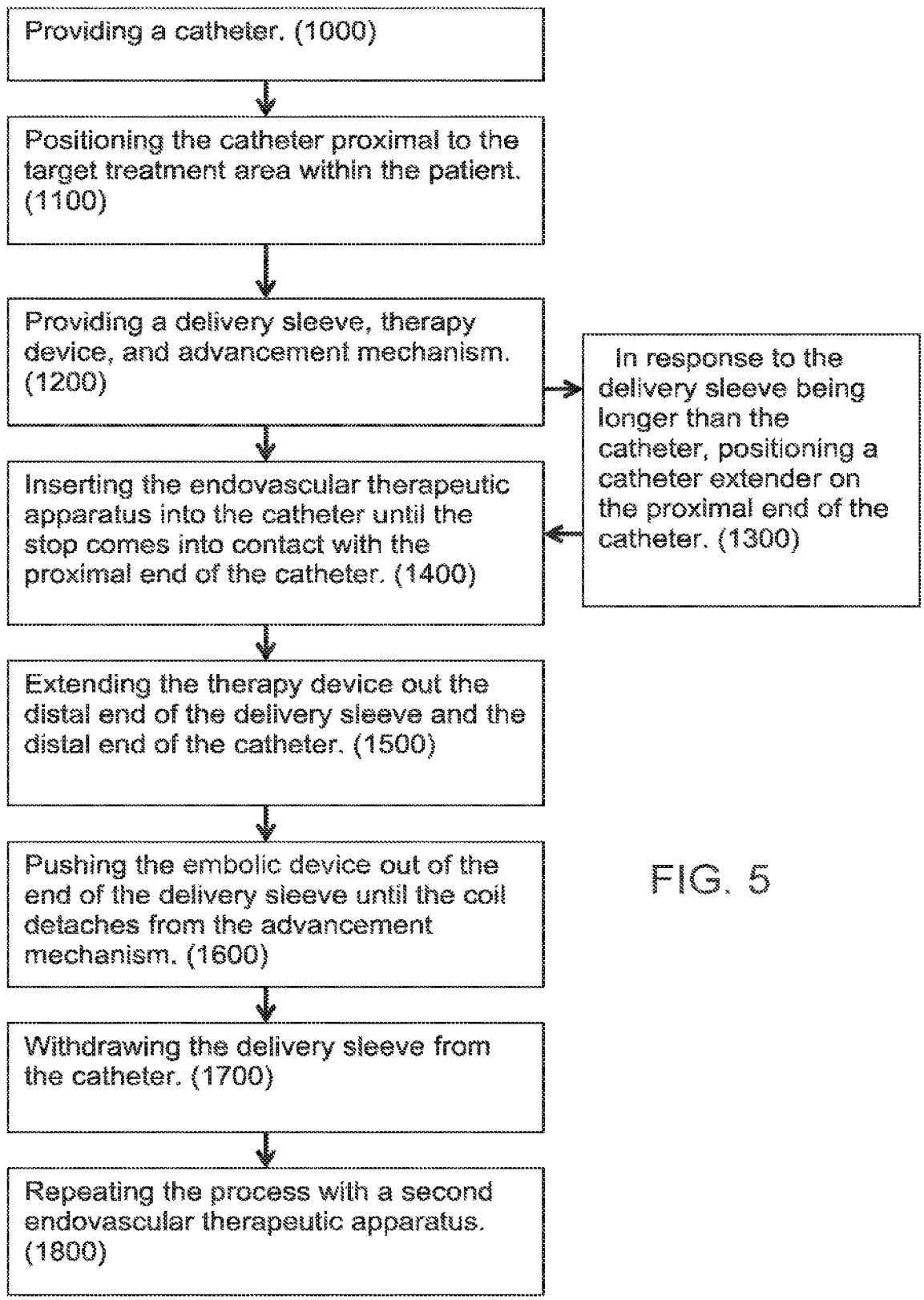
FIG. 5 illustrates a flow chart of a method of using an endovascular system in accordance with various embodiments.

FIG. 5 illustrates a flow chart of a method of using an endovascular system in accordance with various embodiments disclosed herein. A method for delivering a therapeutic treatment to a patient may include providing a catheter having a proximal catheter end and a distal catheter end with a longitudinal catheter lumen extending therebetween (1000). The catheter may be positioned proximal to the target treatment area within the patient (1100). An endovascular therapeutic apparatus having a delivery sleeve, a therapy device, and an advancement device may be provided (1200). The delivery sleeve may have a proximal end and a distal end with a longitudinal lumen extending therebetween. The delivery sleeve may be positioned to be coaxial and movable within the catheter lumen. The therapy device may be located coaxially within the lumen of the delivery sleeve and movable therein. The advancement device may be connected to the therapy device to advance the therapy delivery device through the delivery sleeve into the patient. If the delivery sleeve is longer than the catheter, a catheter extender may be positioned on the proximal end of the catheter (1500). The catheter extender may have a proximal extender end and a distal extender end with a longitudinal extender lumen extending therebetween. The catheter extender may be attached to the proximal catheter end at the distal extender end. The catheter extender may have a length that is approximately equal to the difference in length between the delivery sleeve and the catheter length. When the proximal end of the delivery sleeve is connected to the proximal extender end, the delivery sleeve and the catheter are generally coextensive to the catheter distal end.

The delivery sleeve may include a stop positioned on the proximal end. The stop may be positioned to limit the distance the delivery sleeve is inserted into the catheter. The endovascular therapeutic apparatus may be inserted into the catheter until the stop comes into contact with the proximal end of the catheter (1400). The method may include extending the therapy device out the distal end of the delivery sleeve and further out distal end of the catheter (1500).

The therapy device may be an endovascular embolization coil. The endovascular embolization coil may be detachable coil. The detachable coil may be a polymer coil. The advancement mechanism may be connected to the detachable coil with a connection mechanism that is sized to be compressed or restrained by the delivery sleeve. The detachable coil may remain connected to the advancement mechanism within the delivery sleeve, but once it exits the delivery sleeve, the compression, and thereby the connection, may be released. The detachable coil may be pushed out of the end of the delivery sleeve until the detachable coil disconnects from the advancement mechanism (1600). The delivery sleeve may be withdrawn from the catheter (1700). The process may be repeated by inserting a second endovascular therapeutic apparatus into the catheter (1800).

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention as claimed. Connection references (e.g., attached, coupled, connected, and joined) are to be construed broadly and may include intermediate members between a collection of elements and relative movement between elements unless otherwise indicated. As such, connection references do not necessarily infer that two elements are directly connected or are in fixed relation to each other. The exemplary drawings are for purposes of illustration only and the dimensions, positions, order, and relative sizes reflected in the drawings attached hereto may vary.

The above specification, examples, and data provide a complete description of the structure and use of exemplary embodiments of the invention as claimed. Although various embodiments of the invention as claimed have been described above with a certain degree of particularity, or with reference to one or more individual embodiments, those skilled in the art could make numerous alterations to the disclosed embodiments without departing from the spirit or scope of the invention as claimed. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

We claim:

1. An endovascular apparatus comprising
   a delivery sleeve having a longitudinal lumen extending between a proximal end and a distal end;
   a therapeutic device housed within and extending substantially an entire length of the delivery sleeve;
      wherein the therapeutic device includes one or more detachable polymer endovascular embolization coils;
   an advancement mechanism configured to engage the therapeutic device to advance the therapeutic device into a patient; and
   a stop positioned on the proximal end of the delivery sleeve which is operable to limit a distance the delivery sleeve is inserted into a catheter;
   wherein an outside diameter of the delivery sleeve is sufficiently small such that the delivery sleeve is insertable into the catheter and a diameter of the lumen is sufficiently large such that the lumen is able to coaxially receive the therapeutic device and the advancement mechanism therein but sufficiently small that the delivery sleeve adds longitudinal strength to the therapeutic device.

2. The endovascular apparatus of claim 1, wherein both an inner surface and an outer surface of the delivery sleeve are composed of a material with a low coefficient of friction.

3. The endovascular apparatus of claim 1. wherein the therapeutic device extends approximately to the distal end of the delivery sleeve.

4. The endovascular apparatus of claim 1 further comprising:
   a connection mechanism that connects the advancement mechanism to the therapeutic device,
   wherein the connection mechanism is sized relative to the delivery sleeve such that the connection mechanism is compressed by the delivery sleeve and remains connected while in the delivery sleeve, but once the connection mechanism exits the delivery sleeve the compression, and thereby the connection, is released; and
   wherein the therapeutic device is located coaxially within the delivery sleeve; and the advancement mechanism is connected to a proximal end of the therapeutic device.

5. The endovascular apparatus of claim 1, wherein the stop is a luer connection operable to engage an opposing luer connection on a proximal end of the catheter.

6. An endovascular system comprising
   a catheter having a proximal catheter end and a distal catheter end with a longitudinal catheter lumen extending therebetween;
   a delivery sleeve having a proximal end and a distal end with a longitudinal lumen extending therebetween, wherein the delivery sleeve is coaxial with and movable within the catheter lumen;
a therapeutic device extending substantially an entire length of the delivery sleeve and located coaxially within the lumen of the delivery sleeve and movable therein;
an advancement mechanism connected to the therapeutic device and configured to advance the therapeutic device into a patient; and
a stop positioned on the proximal end of the delivery sleeve which contacts the proximal catheter end, limiting the distance the delivery sleeve is inserted into the catheter; and
a connection mechanism that connects the advancement mechanism to the therapeutic device, wherein the connection mechanism is sized relative to the delivery sleeve such that the connection mechanism is compressed by the delivery sleeve and remains connected while in the delivery sleeve, but once the connection mechanism exits the delivery sleeve the compression, and thereby the connection, is released.

7. The endovascular system of claim 6, wherein the delivery sleeve is made of polytetrafluoroethylene.

8. The endovascular system of claim 6 further comprising:
a catheter extender having a proximal extender end and a distal extender end with a longitudinal extender lumen extending therebetween, wherein the distal extender end is attached to the proximal catheter end, and wherein the delivery sleeve is longer than the catheter.

9. The endovascular system of claim 8, wherein the catheter extender has a length that is approximately a difference in length between an entire length of the delivery sleeve and an entire length of the catheter, so that when the proximal end of the delivery sleeve is connected to the proximal extender end, the delivery sleeve and the catheter are generally coextensive to the distal catheter end.

10. The endovascular system of claim 6, wherein the therapeutic device is a detachable endovascular embolization coil formed of a polymer.

11. The endovascular system of claim 6, wherein the therapeutic device is located coaxially within the delivery sleeve; and
the advancement mechanism is connected to a proximal end of the therapeutic device.

12. The endovascular system of claim 6, wherein:
the advancement mechanism is further connected to a distal end of the therapeutic device; and
the therapeutic device extends approximately to the distal end of the delivery sleeve.

13. A method for delivering a therapeutic treatment to a patient comprising:
providing a catheter having a proximal catheter end and a distal catheter end with a longitudinal catheter lumen extending therebetween;
providing a therapeutic delivery device apparatus comprising:
a delivery sleeve having a proximal end and a distal end with a longitudinal lumen extending therebetween, wherein the delivery sleeve is coaxial and longitudinally movable within the catheter lumen;
a therapeutic device that extends substantially an entire length of the delivery sleeve and enclosed coaxially within the lumen of the delivery sleeve and longitudinally movable therein;
an advancement mechanism connected to the therapeutic device and configured to advance the therapeutic delivery device into a patient;
a stop positioned on the proximal end of the delivery sleeve which contacts the proximal catheter end of the catheter, limiting a distance the delivery sleeve is inserted into the catheter.
inserting the therapeutic delivery device into the catheter until the stop comes into contact with the proximal catheter end; and
wherein the therapeutic delivery device is a detachable polymer endovascular embolization coil.

14. The method of claim 13 further comprising
attaching a catheter extender to the catheter in response to the delivery sleeve being longer than the catheter, wherein
the catheter extender includes a proximal extender end and a distal extender end with a longitudinal extender lumen extending therebetween which is attached to the proximal catheter end via the distal extender end.

15. The method of claim 13, wherein, in the method, the therapeutic delivery device further comprises a connection mechanism; and the method further comprises:
connecting the advancement mechanism to the therapeutic device;
compressing the connection mechanism within the delivery sleeve such that the connection mechanism remains connected while in the delivery sleeve;
releasing the connection mechanism from the delivery sleeve once the connection mechanism exits the delivery sleeve;
pushing the therapeutic device out the end of the delivery sleeve until the compression of the delivery sleeve on the connection mechanism is released and the therapeutic device disconnects from the advancement mechanism; and
withdrawing the delivery sleeve from the catheter and repeating the process with a second therapeutic delivery device.

16. The method of claim 14 further comprising:
determining a difference in length between an entire length of the delivery sleeve and an entire length of the catheter; and
selecting the catheter extender such that a length of the catheter extender is approximately equal to the difference in length so that in response to the proximal end of the delivery sleeve being connected to the proximal extender end, the delivery sleeve and the catheter are generally coextensive to the distal catheter end.

\* \* \* \* \*